United States Patent [19]
Gueret

[11] Patent Number: 6,063,398
[45] Date of Patent: May 16, 2000

[54] COSMETIC OR DERMOPHARMACEUTICAL PATCH CONTAINING, IN AN ANHYDROUS POLYMERIC MATRIX, AT LEAST ONE ACTIVE COMPOUND WHICH IS, IN PARTICULAR, UNSTABLE IN OXIDIZING MEDIUMS, AND AT LEAST ONE WATER-ABSORBING AGENT

[75] Inventor: Jean-Louis H. Gueret, Paris, France

[73] Assignee: L'Oreal, Paris, France

[21] Appl. No.: 08/925,086

[22] Filed: Sep. 8, 1997

Related U.S. Application Data

[63] Continuation-in-part of application No. 08/715,822, Sep. 19, 1996, abandoned.

[30] Foreign Application Priority Data

Sep. 20, 1995 [FR] France ................................. 95 11030

[51] Int. Cl.$^7$ .............................. A61L 15/24; A61L 15/26
[52] U.S. Cl. ............................................ 424/443; 424/466
[58] Field of Search ............................................... 424/443

[56] References Cited

U.S. PATENT DOCUMENTS

| | | | |
|---|---|---|---|
| 5,213,794 | 5/1993 | Fritsch et al. | 424/78.01 |
| 5,252,334 | 10/1993 | Chiang et al. | 424/443 |
| 5,397,848 | 3/1995 | Yang et al. | 525/477 |

FOREIGN PATENT DOCUMENTS

| | | |
|---|---|---|
| 137 278 | 4/1985 | European Pat. Off. . |
| 190 814 | 8/1986 | European Pat. Off. . |
| 196 769 | 10/1986 | European Pat. Off. . |
| 309 309 | 3/1989 | European Pat. Off. . |
| 379 933 | 8/1990 | European Pat. Off. . |
| 412 869 | 2/1991 | European Pat. Off. . |
| 93/19789 | 10/1993 | WIPO . |

*Primary Examiner*—Peter F. Kulkosky
*Attorney, Agent, or Firm*—Nixon & Vanderhye P.C.

[57] ABSTRACT

A cosmetic or dermopharmaceutical patch containing, in an anhydrous polymeric matrix, at least one active compound, in particular a compound unstable in oxidizing medium, and at least one water-absorbing agent is disclosed.

19 Claims, No Drawings

COSMETIC OR DERMOPHARMACEUTICAL PATCH CONTAINING, IN AN ANHYDROUS POLYMERIC MATRIX, AT LEAST ONE ACTIVE COMPOUND WHICH IS, IN PARTICULAR, UNSTABLE IN OXIDIZING MEDIUMS, AND AT LEAST ONE WATER-ABSORBING AGENT

The present application is based on FR 9511030, filed Sep. 20, 1995, and is a continuation-in-part of U.S. application Ser. No. 08/715,822 filed Sep. 19, 1991 now abandoned, the entire contents of each of which are incorporated herein by reference.

The present invention concerns a patch allowing the controlled release, on the skin surface, of at least one cosmetically or dermopharmaceutically-active compound, in particular a compound unstable in oxidizing mediums.

In the present description, the term "patch" designates a composite, layered structure which, when applied on the skin, allows release of an active product on the surface thereof.

When the active compound is unstable in oxidizing mediums, the compound may undergo degradation after sufficient contact time with an oxidizing medium, for example by hydrolysis after several hours in an aqueous medium.

Conventional practice encompasses patches allowing, by means of transdermal migration, penetration of the active compounds.

These patches normally have a structure comprising several successive layers in the following order: a first-so-called support layer, which is normally occlusive, that is, composed of a material impermeable to the active compound, so as to prevent the evaporation thereof and facilitate transdermal migration; a second, so-called storage layer fastened to the support layer and containing the active compound and capable of placement directly in contact with the skin; potentially, to facilitate attachment of the patch to the skin, a layer of an adhesive material applied to the surface of the storage layer and permeable to the active compound; and finally, a detachable protective layer which hermetically covers the storage layer so as to protect it from any external contamination during storage prior to use of the patch.

EP 412 869, most especially, discloses a patch structure formed by an occlusive support layer and comprising, attached to the latter, a storage layer in a silicone polymer matrix incorporating, in the dispersed state, aqueous gel particles containing at least one cosmetically- or pharmaceutically-active compound. While this type of patch is more particularly suited to the delivery of active compounds exhibiting little sensitivity to oxidation phenomena, its effectiveness remains, however, poor as regards active compounds unstable in oxidizing mediums.

In this latter case, because it is contained in the aqueous gel particles, the active compound deteriorates rapidly as a result of oxidation in contact with the medium.

EP Application No. 190 814 describes an occlusive bandage composed of a flexible layer of polyurethane foam having closed cells and containing, in the foam lattice, approximately 5 to 50% by weight in relation to the foam of at least one agent dispersible in water, inflatable in water, and/or water-absorbent and, potentially, in a proportion of less than 5% by weight of at least one pharmaceutically-active compound.

This type of bandage, which is especially well suited to treating wounds, has the disadvantage of existing as a closed-cell foam, so that release of the active compound, when present, occurs slowly and takes place only when the exudate from the wound has penetrated within the foam. It will, accordingly, be understood that, in accordance with Application No. EP 190 814, when placed on a wound the bandage acts mainly to dry the wound by virtue of the migration of the exudate, which then reacts with the water-dispersible, water-inflatable, and/or water absorbent agent.

The potential presence of an active compound such as an antibiotic, an anti-microbial agent, or an antiseptic is thus of secondary importance, since it is not intended to be diffused directly on the wound, but to act on the exudate absorbed by the closed-cell foam.

In addition, Application No. EP 196,769 describes a transdermal patch incorporating a support layer, a storage layer comprising a solid polymeric matrix in disk form in which a suitable quantity of a pharmaceutical compound is dispersed and to which an adhesive layer is attached, this layer containing an efficacious quantity of at least one agent which increases transdermal migration of the pharmaceutical compound.

While it allows improved availability of the pharmaceutcially-active compound, this type of patch is difficult to manufacture, since the compound in the adhesive layer intended to increase transdermal migration must be selected based on the nature of the active compound, and this compound, which comes into contact with the skin, must cause no allergic reaction.

The present invention makes it possible to solve the problems encountered in the state-of-the-art when the active compound is unstable in oxidizing mediums.

In fact, it was found, entirely surprisingly and unexpectedly, that, by dispersing uniformly in a specific hydrophobic matrix at least one cosmetically- or dermopharmaceutically-active compound which is, in particular, unstable in oxidizing mediums, with certain water-absorbing agents, it was possible to produce a patch containing an anhydrous storage layer, but which nevertheless allowed a high degree of controlled release of the active compound, with no deterioration of the latter.

It was found that, after removing the detachable protective layer, the patch could be placed directly on the skin surface to be treated, but without the necessity, in order to achieve the sought-after effect, of moistening either the area of skin requiring treatment or the patch itself.

The at least partially occlusive support layer produces, on the area of skin on which the patch is placed, condensation of perspiration, thus allowing it to be moistened sufficiently to permit release of the active compound by means of the particles of the water-absorbent agent dispersed therein.

In fact, in contact with skin moisture (or, potentially, in the presence of water spread on the skin or storage layer) the particles of the water absorbent agent react, then gradually release the particles of the active compound.

Accordingly, the present invention concerns a cosmetic or dermopharmaceutical patch for the controlled release of at least one cosmetically- or dermopharmaceutically-active compound on the skin, this patch comprising a storage layer attached to a support layer, said storage layer being formed from a hydrophobic polymeric matrix in which particles of at least one active compound potentially unstable in an oxidizing medium are uniformly dispersed and from particles of at least one water-absorbing agent, said storage layer being anhydrous and compact.

The term "compact" signifies, according to the invention, that the storage layer exists as a dense mass which, accordingly, does not incorporate alveolated or cellular gaps, in contradistinction to the storage layer in accordance with Application No. EP 180 814, which exists as a polyurethane foam or, more precisely, expanded polyurethane foam.

Since the particles of active compound and water-absorbing agent are dispersed uniformly in the storage layer, at least one portion of said particles are present on the surface of the storage layer coming into direct contact with the skin, thereby making possible, after removing the detachable protective layer, the especially effective and rapid release of the active compound, a release that could not be obtained according to the state of the art.

In the patches according to the invention in question, the hydrophobic polymeric matrix is, for example, based on a silicone polymer or a polyester or polyether polyurethane.

When the polymeric matrix is silicone polymer-based, the silicone prepolymer is preferably chosen from linear organopolysiloxanes substituted on the silicon atom by various groups, the terminal silicon atoms being trisubstituted. These organopolysiloxanes are described, most notably, in U.S. Pat. Nos. 2,541,137, 2,723,966, 2,863,846, 2,890,188, 2,927,907, 3,002,951, and 3,035,016, the entire contents of which are incorporated herein by reference.

As silicone prepolymer, special preference is given to polydimethylsiloxanes corresponding to the formula:

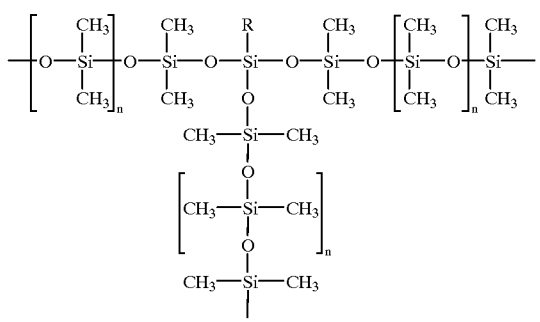

where:
R represent an alkyl or alkoxy group containing 1 to 7 atoms of carbon or a vinyl or phenyl group, and in which n is between approximately 100 and 5,000.

The silicone prepolymer can be cross-linked, preferably at moderate temperatures such as ambient temperature, using a biologically-acceptable cross-linking catalyst in the resulting polymeric matrix, this catalyst being compatible with the active compound dispersed in the latter.

The term "cross-linking catalyst" according to the invention signifies the combination of a cross-linking agent and a catalyst.

When the silicone prepolymer comprises hydroxy groups, such as terminal hydroxy groups, the cross-linking agent may be tetrapropoxysilane [Si—(O—CH$_3$—CH$_2$—CH$_3$)$_4$] in combination with a tin-based catalyst.

When the silicone prepolymer comprises vinyl groups, the latter can be cross-linked in the presence of a dimethylsilicone polymer in combination with a catalyst, such as a platinum-based catalyst.

Among the silicone prepolymers especially preferred according to the invention, mention may be made of those under the trade names SILASTIC 382®, Q7-4635®, Q7-4650®, Q7-4735®, Q7-4750®, Q7-4765®, MDX-4-4210®, and DC 3.6486® sold by Dow Corning.

When the polymeric matrix is polyurethane-based, it is produced from a polyester-polyalcohol or polyether-polyalcohol prepolymer known in the state of the art.

Polyesters-polyalcohols include those produced by reacting bi- or trifunctional alcohols on acids, such as adipic acid, terephthalic acid, and, more generally, all other multifunctional acids. Polyether-polyalcohols include those produced by alkylation, by reacting diols such as ethylene glycol or propylene glycol, or polyalcohols such as trimethylolpropane, glycerol, pentaerythritol, sorbitol, etc., with oxides such as ethylene oxide, propylene oxide, or mixtures thereof.

The polyaddition agent used for forming polyurethanes is an isocyanate or polyisocyanate, in particular toluene diisocyanate, 1,1'-diphenylmethane diisocyanate, 1,5-naphthalene diisocyanate or isophorone diisocyanate.

The cross-linking catalyst or polyaddition agent is preferably used in a quantity such that the cross-linking or polyaddition is not complete, so that the storage layer incorporates a satisfactory self-adhesive capability in order, advantageously, to avoid the subsequent covering of the support layer with an adhesive layer.

It will be noted, however, that the patches according to the invention may not necessarily adhere to the skin surface.

In fact, depending on the application time, they may either be held in place by the person undergoing treatment, or used to massage a determinate region of the skin requiring treatment.

In the patches according to the invention in question, the cosmetically- or dermopharmaceutically-active compound may, for example, be vitamin C, vitamin A or retinol, vitamin F (essential fatty acids), enzymes, and antibiotics such as clindamycin phosphate.

Among the water-absorbing agents potentially present in the hydrophobic polymeric matrix in the dispersed state, mention may preferably be made of superabsorbent cross-linked polyacrylates exhibiting a high rate of swelling in water, such as those sold by the NORSOLOR Company under the trade name "Aquakeep"®; polyvinyl alcohol; carboxyvinyl polymers such as those sold by the Goodrich Company under the trade name "Carbopol"®; semi-synthetic derivatives of cellulose, such as carboxymethylcellulose; natural substances such as starches, natural gums (guar gum, gum arabic, gum tragacanth), casein, phytocolloids (carragenates, alginates, agar—agar), cotton fibers, and geletin.

Special preference is given to the use, according to the invention, of superabsorbent cross-linked polyacrylates, whose presence in the dispersed state in the hydrophobic, polymeric matrix promote, after hydration, improved contact with the particles of active compound.

In accordance with a special embodiment, the water-absorbing agent may also be particles of freeze-dried or sprayed emulsion in powder form, and these articles may contain at least one active substance.

Preferably, the cosmetically- or dermopharmaceutically-active compound exists in a proportion of between about 0.2 and 48% by weight, and the water-absorbing agent, in a proportion of between about 0.1 and 30% by weight, and preferably 0.5 and 10% of the total weight of the storage layer, provided that the proportion of the mixture of the active compound and of the water-absorbing agent preferably ranges between 15 and 60% by weight of the total weight of the storage layer.

The cosmetically- or dermopharmaceutically-active compound and the water-absorbing agent exist in the dispersed state in the polymeric matrix as particles having an average size of between about 0.2 μm and 1.5 mm, said particles being dispersed uniformly and randomly in the polymeric matrix composing the storage layer.

Because of this random dispersion in the polymeric matrix, the patches according to the invention allow incorporation, in the dispersed state in the polymeric matrix, various active compounds which are not only unstable themselves, but also mutually incompatible.

This embodiment proves especially advantageous when at least two mutually-incompatible active compounds are dispersed within the polymeric matrix, but produce a synergistic effect when released and in contact with the skin.

This is true, for example, when particles of vitamin C combined with enzyme particles are dispersed in the polymeric matrix.

Furthermore, the polymeric matrix may also contain additional cosmetic or dermopharmaceutical ingredients, such as emollient oils and components producing a tensor effect, such as soy or wheat protein powders.

In addition, the polymeric matrix may advantageously contain an effervescent agent, such as sodium bicarbonate or carbonate, so that effervescence can promote the action of the active compound released from the storage layer.

Finally, to increase yield strength of the polymeric matrix, the storage layer may incorporate a framework composed, for example, of a sheet of a perforate plastic material, a sheet of a non-woven fabric, or a net, the non-woven sheet or net being composed of natural or synthetic fibers, such as polyamide, as described in French Patent No. 92-05623 (FR-A-2620914), the entire contents of which are incorporated herein by reference.

The support, or occlusive, layer of the patches according to the invention may be made of any suitable material impermeable to the active compound contained in the adjoining storage layer.

The support layer acts not only to support the storage layer, but also to serve as the protective covering for the latter.

It may be of the same size as the storage layer or larger, so that it extends beyond the periphery of the storage layer and outward, in such a way that the surface enclosing the storage layer may potentially incorporate adhesive means.

Materials suitable for the support layer include high- and low-density polyethylene films, polypropylene films and films composed of polyvinyl chloride, polyester, such as ethylene polyphthalate, ethylene/vinyl acetate copolymers, and polyurethane.

These materials may also exist in stratified form, with at least one sheet of a metal such as aluminum. The support layer may be of any suitable thickness allowing it to perform the desired support and protection functions. The thickness of the support layer preferably ranges between approximately 0.2 and 1.5 mm.

The patches according to the invention may be protected by virtue of a detachable or peelable, protective layer adjacent to the storage layer and/or by enclosure in suitable packaging which is, in particular, water- and steam-impermeable.

When the storage layer is protected by a detachable layer, the latter is removed at the time of use. It may be made of any material impermeable to the active compound and to any other component in the polymeric matrix. Usable materials preferably include a silicone-coated sheet of paper or a sheet of thermoplastic material treated to make it anti-adhesive, for example using a varnish. Preferably, this detachable protective layer is made of polyethylene.

The patches according to the present invention may, conventionally, be cut out in a suitable shape corresponding to the region of the skin surface to be treated, for example as a mask to be placed on the face and, in particular, for placement over the contours of the eyes, the bags under the eyes, the forehead, and the nose (for protection from the sun). Of course, the patches according to the invention may be cut out in any other shape needed for placement on a determinate region of the body.

The patches incorporating this structure and cut out in this way may be used, after removal of the detachable protective layer, on a surface of the skin to be treated, by placing them directly on skin on which the water from perspiration allows the desired release of the cosmetically- or dermopharmaceutically-active compound. They may also be preliminary soaked in water for between about 5 and 30 seconds, or they can be placed on the skin after preliminary moistening, for example with a sponge.

It has, in fact, been found, surprisingly and unexpectedly, that water from perspiration alone advantageously causes release of the active compound on the surface of the skin to be treated, this release emanating from the hydrophobic polymeric matrix containing said compound.

In the patches according to the invention, the polymeric matrix forming the storage layer is prepared by intimate mixing, while stirring, the silicone or polyurethane prepolymer, the cosmetically- or dermopharmaceutically-active compound, and the water-absorbing agent, both of which are in particle form, as well as the optional compounds mentioned above.

Either a cross-linking catalyst, if the prepolymer is a silicone polymer, or an isocyanate or polyisocyanate, if the prepolymer is a polyester-polyalcohol or a polyether-polyalcohol, is added at low temperature, normally at ambient temperature, to the mixture thus produced.

The mixture is then fed into a hopper and poured, for example, on a sheet of polyethylene, which makes up the detachable or peelable protective film of the patch. Down line from the hopper is a scraper making it possible to even out the thickness of the storage layer of the polymeric layer, this thickness normally being between 01. mm and 12 mm.

Next, a framework sheet as described above is put on from a roller, then, prior to finishing, a sheet of the support, or occlusive, layer, which may also be a sheet of polyethylene also taken from a roller is put in place.

Polymerization or polyaddition preferably occurs at ambient temperature, so as not to cause deterioration of the active compound or compounds.

After finishing and before polymerization or polyaddition is completed, the composite structure produced may be cut out immediately to the desired shapes, thereby giving pinched edges preventing any running.

In general, polymerization or polyaddition is complete after approximately 24 hours at ambient temperature.

The present invention also concerns the use of a patch as described above, the invention being characterized by the fact that the patch is put on dry and occlusively on a region of the skin surface to be treated.

The patches according to the invention make it possible to produce an effect very rapidly, normally in about 5 to 10 minutes after application.

The following examples illustrate the present invention.

EXAMPLE 1

2 g sodium carbonate and 2 g vitamin C were added to 8 g powdered polyacrylate (Aquakeep® sold by the Norsolor Company). Next, the mixture was micronized to the desired grain size, and 43 g organopolysiloxane, or DC3.6486®, sold by the Corning Company were added. While stirring at 1,500 rpm, 1.7 g "Medical Grade Curing Agent" cross-linking catalyst were added, and stirring continued for several minutes.

The product homogenized in this way was fed into a hopper and spread using a scraper in a layer 0.8 mm thick on a polyethylene sheet having a thickness of 200 μm. This sheet could be preliminary surface-treated to reduce adhesiveness. A framework consisting of a polyamide or polyethylene net whose meshwork had openings measuring 1 mm and which had a thickness of 0.3 mm was incorporated into the polyethylene sheet treated in this way.

A polyethylene film (not undergoing any anti-adhesiveness treatment) 30 μm thick was deposited; this film constituted the support or occlusive layer of the patch, and the unit underwent finishing. In this way, the product obtained was a unit comprising an occlusive support layer and a self-adhesive storage layer formed from a partially cross-linked silicone polymer matrix, this unit further comprising a detachable protective layer.

Using this unit, various patch shapes could be cut out depending on the desired applications.

After being cut out, the patches were then packed in polyethylene bags. During use and after removal of the detachable protective layer, the patch was place directly on the outline of an eye, for example for about 7 minutes. After removing the patch, it was observed visually that the outline of the eye treated with the patch, which contained vitamin C, had an appreciably lighter color and a smoother and more rested appearance than that of the untreated eye.

EXAMPLE 2

To 10 g of powdered polyacrylate ("Aquakeep®" sold by NORSOLOR COMPANY) 5 g of sodium carbonate and 5 g of vitamin C are added. Then the mixture was micronized to the desired grain size and next a mixture of 70 g polyisocyanate ("Desmodur®" sold by BAYER COMPANY) and 10 g of polyol ("Desmophen®" sold by BAYER COMPANY) is added.

The obtained mixture is then homogenized under stirring at 1,500 rpm.

The homogenized product is then introduced into a hopper and spread using a scraper in a layer 0.8 mm thick on a polyethylene sheet having a thickness of 200 μm. This sheet could be preliminary surface treated to reduce adhesiveness. A framework consisting of a polyamide or polyethylene net whose meshwork had openings measuring 1 mm and which had a thickness of 0.3 mm was incorporated into the polyethylene sheet treated in this way.

A polyethylene film (not undergoing any anti-adhesiveness treatment) 30 μm thick was deposited; this film constituted the support or occlusive layer of the patch, and the unit underwent finishing. In this way, the product obtained was a unit comprising an occlusive support layer and a self-adhesive storage layer formed from a polyurethane polymer matrix, this unit further comprising a detachable protective layer.

Using this unit, various patch shapes could be cut out depending on the desired applications.

After being cut out, the patches were then packed in polyethylene bags. During use and after removal of the detachable protective layer, the patch was placed directly on the outline of an eye, for example, for about 15 minutes. After removing the patch, it was observed visually that the outline of the eye treated with the patch, which contained vitamin C, had an appreciably lighter color and a smoother and more rested appearance than that of the untreated eye.

I claim:

1. A cosmetic or dermopharmaceutical patch comprising at least one cosmetically or pharmaceutically active compound, which is unstable in an oxidizing media, said patch comprising a support layer on which an anhydrous storage layer is attached, said storage layer being formed from a hydrophobic polymer selected from the group consisting of a silicone polymer and a polyester or polyether polyurethane, said storage layer containing particles of the active compound, which is unstable in said oxidizing media, together with particles of at least one water-absorbing agent selected from the group consisting of superabsorbent cross-linked polyacrylates, polyvinyl alcohol, carboxyvinyl polymers, semi-synthetic cellulose derivatives, starches, guar gum, gum arabic, gum tragacanth, casein, phytocolloids, cotton fibers and gelatin, said particles having an average size of between 0.2 μm and 1.5 mm and being homogeneously dispersed within the storage layer, said storage layer being compact and homogeneous and said patch being optionally protected with a protective layer.

2. Patch according to claim 1, wherein said patch is self-adhering.

3. Patch according to claim 1, wherein said patch is non-adhesive.

4. Patch according to claim 1 wherein the silicone polymer-based storage layer is produced by cross-linking a linear substituted organopolysiloxane on the silicon atom by means of groups selected from the group consisting of an alkyl group having $C_1$–$C_6$, an aryl group and an aralkyl group having $C_1$–$C_2$, the terminal silicon atoms being trisubstituted.

5. Patch according to claim 4, wherein the organopolysiloxane corresponds to the general formula:

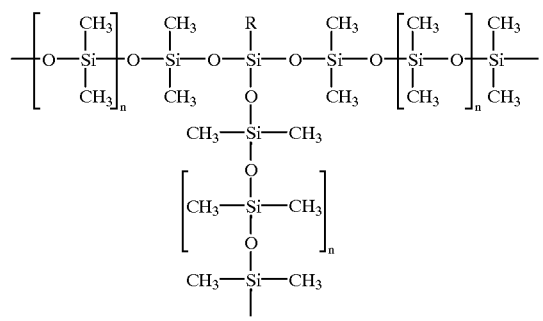

where:
R represents an alkyl or alkoxy group containing 1 to 7 atoms of carbon and a vinyl or phenyl group, and where n ranges between about 100 and 5,000.

6. Patch according to claim 1, wherein the polyurethane-based polymeric matrix is produced by polyaddition of a polyester/polyalcohol or a polyether/polyalcohol in the presence of an isocyanate or polyisocyanate selected from the group consisting of toluene diisocyanate, 4,4'-diphenylmethane diisocyanate, 1,5-NAPHTHALENE diisocyanate, and isophorone diisocyanate.

7. Patch according to claim 1, wherein the cosmetically- or dermopharmaceutically-active compound is selected from the group consisting of vitamin C, vitamin A, vitamin F, enzymes, and antibiotics.

8. Patch according to claim 1, wherein the water-absorbing agent exists as particles of freeze-dried or sprayed emulsions in powder form potentially containing at least one active substance.

9. Patch according to claim 1, wherein the active compound is present in the storage layer in a proportion of between about 0.2 and 48% by weight of the total weight of said layer.

10. Patch according to claim 1, wherein the water-absorbing agent is present in the storage layer in a proportion of between approximately 0.1 and 30% by weight of the total weight of said layer.

11. A process for treating the skin comprising applying to the surface of the skin to be treated a cosmetic or dermopharmaceutical patch according to claim 1.

12. Patch according to claim 1 wherein the proportion of the mixture of particles of the active compound and water-absorbing agent is between 15 and 60% by weight of the total weight of the storage layer.

13. Patch according to claim 1, wherein the storage layer further comprises at least one cosmetic or dermopharmaceutical ingredient selected from the group consisting of emollient oils and soy or wheat protein powders.

14. Patch according to claim 1, wherein the storage layer further comprises an effervescent agent selected from the group consisting of sodium bicarbonate and sodium carbonate.

15. Patch according to claim 1, wherein the storage layer further comprises a framework selected from the group consisting of a sheet of a perforated plastic material, a perforated sheet of a non-woven fabric made of natural or synthetic fibers, and a net made of natural or synthetic fibers.

16. Patch according to claim 1, wherein the thickness of the storage layer is between about 0.1 mm and 12 mm.

17. Patch according to claim 1, wherein the support layer consists of a polymer selected from the group consisting of high- and low-density polyethylenes, polypropylenes, polyvinyl chloride, ethylene and vinyl acetate copolymers, polyesters, and polyurethanes.

18. Patch according to claim 1, wherein the thickness of the support layer ranges between about 0.2 mm and 1.5 mm.

19. The process of claim 11 wherein the surface of the skin is moistened.

* * * * *